(12) United States Patent
Mulqueen et al.

(10) Patent No.: US 9,204,631 B2
(45) Date of Patent: Dec. 8, 2015

(54) MICROENCAPSULATION

(75) Inventors: Patrick Joseph Mulqueen, Bracknell (GB); Philip Taylor, Bracknell (GB); David Ian Gittins, St Austell (GB)

(73) Assignee: IMERYS MINERALS LIMITED, Par Cornwall (GB)

( * ) Notice: Subject to any disclaimer, the term of this patent is extended or adjusted under 35 U.S.C. 154(b) by 0 days.

(21) Appl. No.: 12/922,371

(22) PCT Filed: Mar. 13, 2009

(86) PCT No.: PCT/GB2009/000680
§ 371 (c)(1),
(2), (4) Date: May 3, 2011

(87) PCT Pub. No.: WO2009/063257
PCT Pub. Date: May 22, 2009

(65) Prior Publication Data
US 2011/0200658 A1    Aug. 18, 2011

(30) Foreign Application Priority Data

Mar. 13, 2008    (GB) .................................. 0804700.3

(51) Int. Cl.
| | | |
|---|---|---|
| *A01N 25/28* | (2006.01) | |
| *B01J 13/04* | (2006.01) | |
| *B01J 13/14* | (2006.01) | |
| *A61Q 17/00* | (2006.01) | |

(52) U.S. Cl.
CPC ............... *A01N 25/28* (2013.01); *B01J 13/04* (2013.01); *B01J 13/14* (2013.01); *A61Q 17/00* (2013.01); *Y10S 977/773* (2013.01)

(58) Field of Classification Search
None
See application file for complete search history.

(56) References Cited

U.S. PATENT DOCUMENTS

| | | | | |
|---|---|---|---|---|
| 4,056,610 | A * | 11/1977 | Barber et al. ................... | 424/419 |
| 6,149,843 | A * | 11/2000 | Scher et al. ..................... | 264/4.1 |
| 2002/0004059 | A1 | 1/2002 | Van Koppenhagen et al. | |
| 2002/0040065 | A1* | 4/2002 | Scher et al. ..................... | 516/98 |
| 2004/0034123 | A1* | 2/2004 | Hoefler .......................... | 523/216 |
| 2004/0138339 | A1* | 7/2004 | Freeman et al. ............... | 523/200 |
| 2011/0200658 | A1 | 8/2011 | Mulqueen et al. | |

FOREIGN PATENT DOCUMENTS

| | | |
|---|---|---|
| CA | 2133779 | 4/1995 |
| EP | 0 225 799 A2 | 6/1987 |
| EP | 0 463 926 A1 | 1/1992 |
| EP | 0 539 142 A1 | 4/1993 |

(Continued)

OTHER PUBLICATIONS

BP Binks. "Particles as Surfactants—Similarities and Differences. Current Opinion in Colloid & Interface Science." vol. 7, 2002, pp. 21-41.*

(Continued)

*Primary Examiner* — Isaac Shomer
(74) *Attorney, Agent, or Firm* — Finnegan, Henderson, Farabow, Garrett & Dunner, L.L.P.

(57) ABSTRACT

A process for making microcapsules comprising i) forming a solution of a cross-linker in a liquid; ii) forming a slurry of a surface-modified particulate inorganic material in an aqueous medium; and iii) dispersing the solution of step i) in the slurry of step ii) and causing or allowing the cross-linker to react with the surface-modified particulate inorganic material so as to form a cross-linked microcapsule wall.

18 Claims, 11 Drawing Sheets

(56) References Cited

FOREIGN PATENT DOCUMENTS

| JP | 06-170214 | 6/1994 |
|---|---|---|
| WO | WO 96-33611 | 10/1996 |
| WO | WO 97-44125 | 11/1997 |
| WO | WO 03-090540 A1 | 11/2003 |
| WO | WO 2008-032022 A2 | 3/2008 |
| WO | WO 2009/063257 A2 | 5/2009 |

OTHER PUBLICATIONS

A Katti, N Shimpi, S Roy, H Lu, EF Fabrizio, A Dass, LA Capadona, N Leventis. "Chemical, Physical, and Mechanical Characterization of Isocyanate Cross-linked Amine-Modified Silica Aerogels." Chem. Mater. vol. 18, 2006, pp. 285-296.*

Office Action issued in related Chinese Application No. 200980108792.1, dated Nov. 2, 2012.

Translation of Office Action issued in related Eurasian Patent Application No. 201001426, dated Nov. 28, 2012.

Translation of Office Action issued in related Japanese Application No. 2010-550261, dated Jul. 3, 2012.

Invitation to Respond to Written Opinion issued in related Singapore Application No. 201006050-7, dated Sep. 27, 2011.

Invitation to Respond to Written Opinion issued in related Singapore Application No. 201006050-7 dated Jul. 26, 2012.

International Search Report for related International Application No. PCT/GB2009/000680, dated Aug. 31, 2010.

Bon, Stefan A. F., and Chen, Tao, "Pickering Stabilization as a Tool in the Fabrication of Complex Nanopatterned Silica Microcapsules", American Chemical Society, Langmuir, vol. 23, 2007, pp. 9527-9530.

Yang, Fei; Liu, Shangying; Xu, Jian; Lan, Qiang; Wei, Fang; and Sun, Dejun; "Pickering emulsions stabilized solely by layered double hydroxides particles: The effect of salt on emulsion formation and stability", Elsevier, Journal of Colloid and Interface Science, vol. 302, 2006, pp. 159-169.

Office Action for related Mexican Patent Application No. MX/a/2010/009852, issued Apr. 1, 2014, 3 pages.

Office Action issued for related Canadian Patent Application No. 2,717,262, dated Feb. 12, 2015.

Examination Report issued for related European Patent Application No. 09 700 032.7, dated Apr. 8, 2015.

* cited by examiner

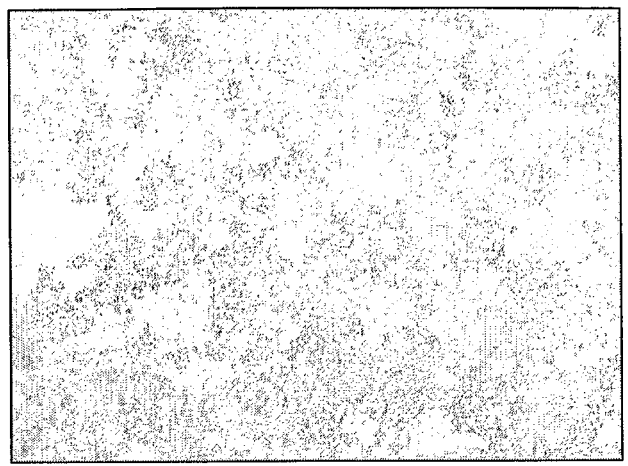
FIG. 1   20μm
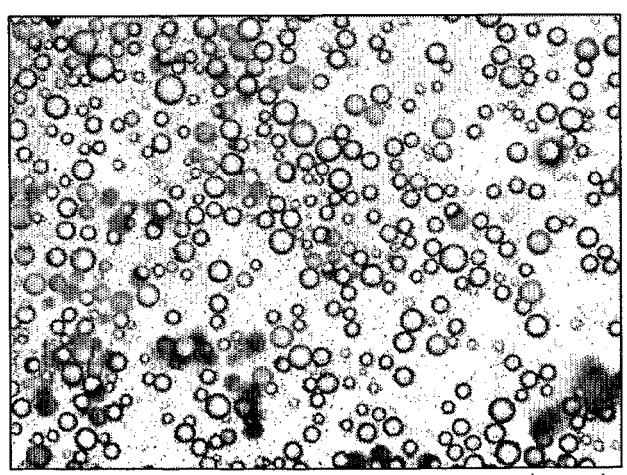
FIG. 2   50μm

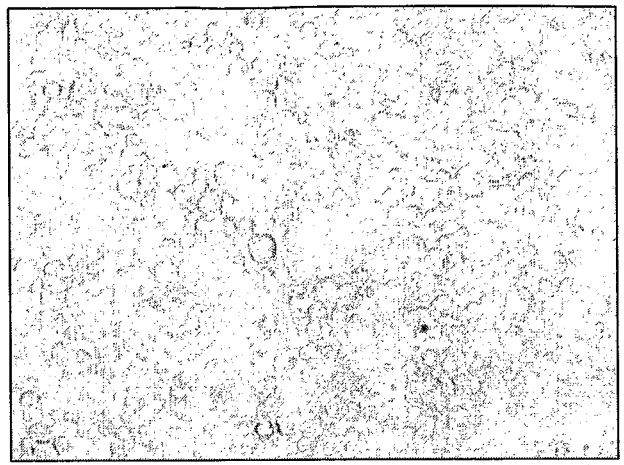
FIG. 2a  100μm
FIG. 2b  20μm

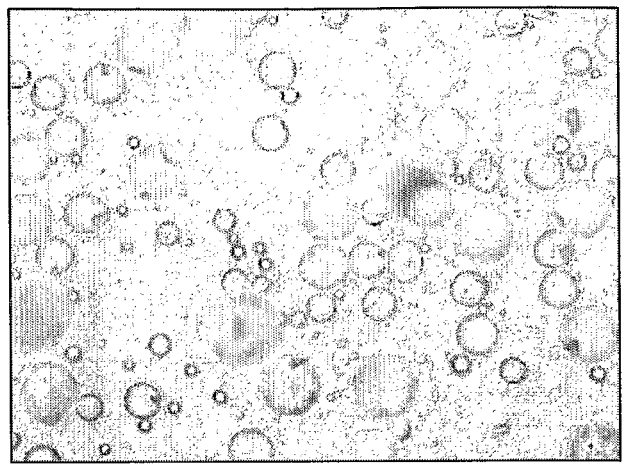
FIG. 3  20μm
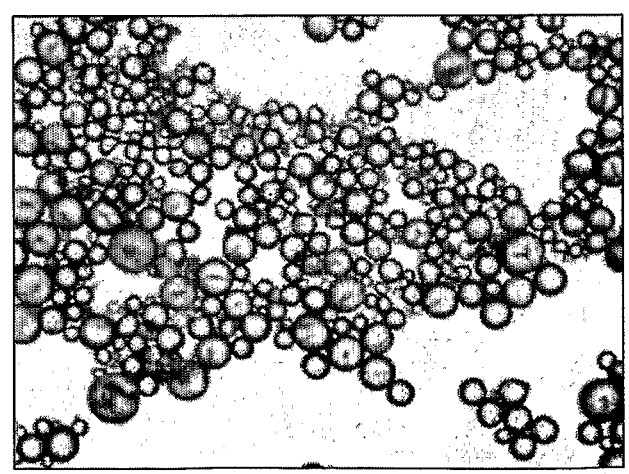
FIG. 3a  50μm

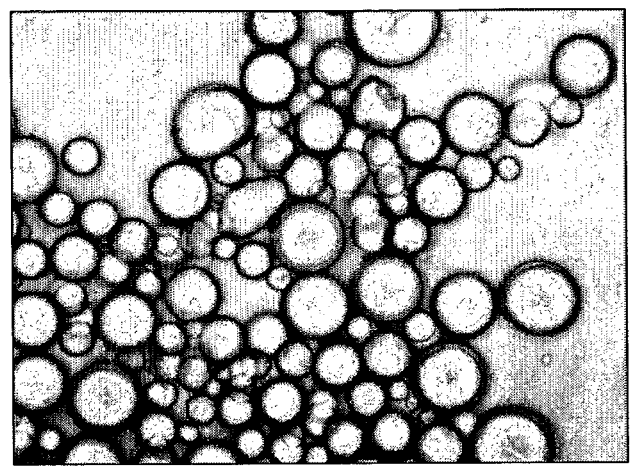
FIG. 3b  20μm
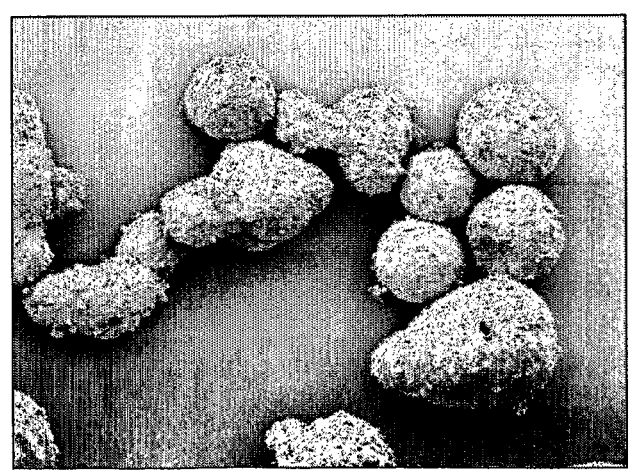
FIG. 4  20μm

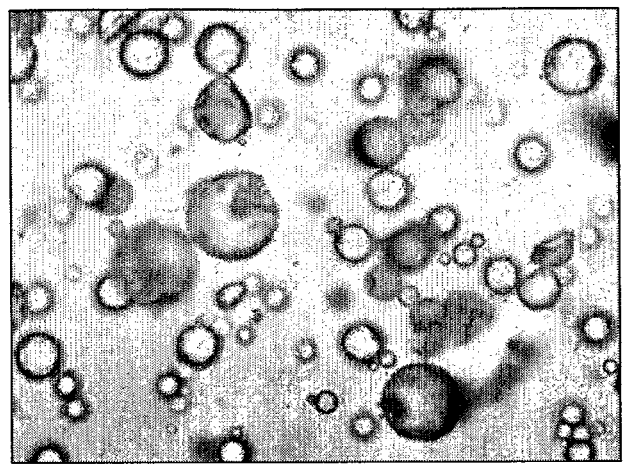
FIG. 5   20μm
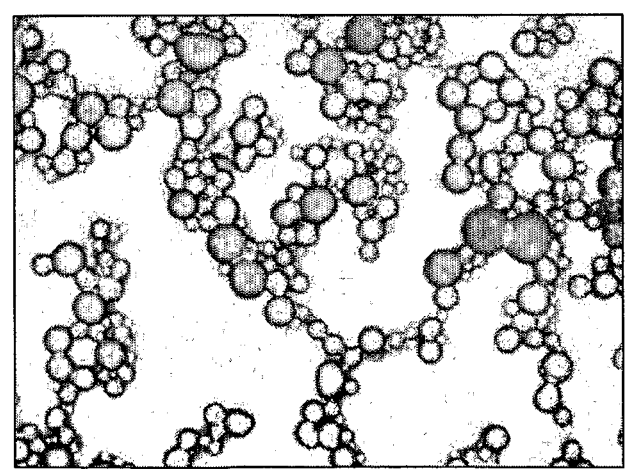
FIG. 5a   50μm

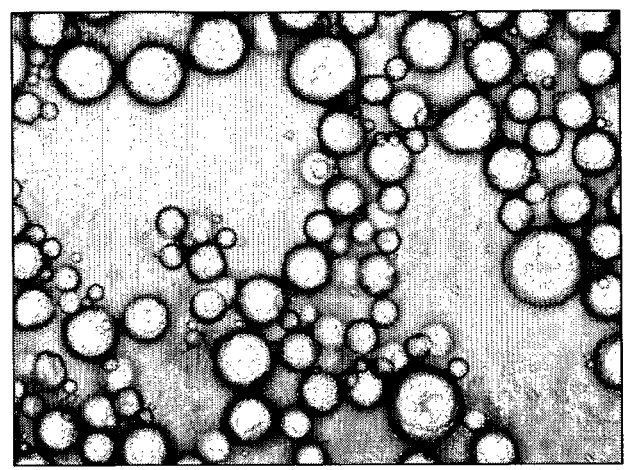
FIG. 5b  20μm
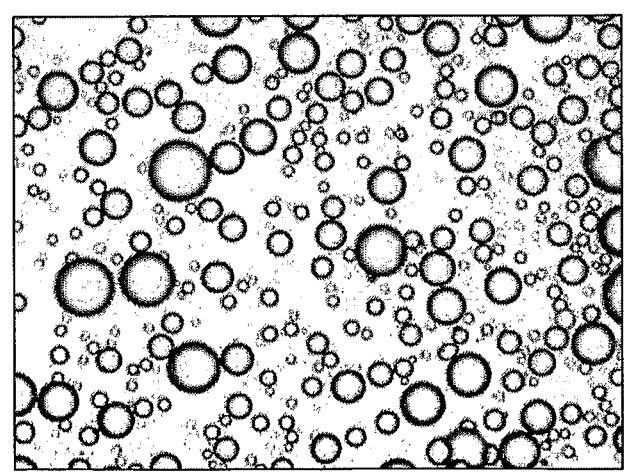
FIG. 6a  100μm

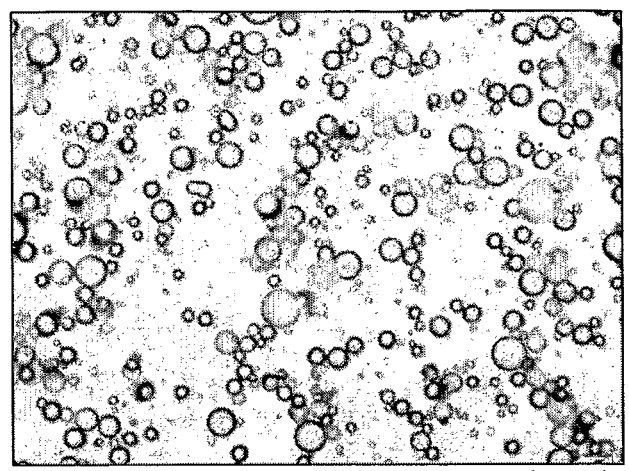
FIG. 11  50μm
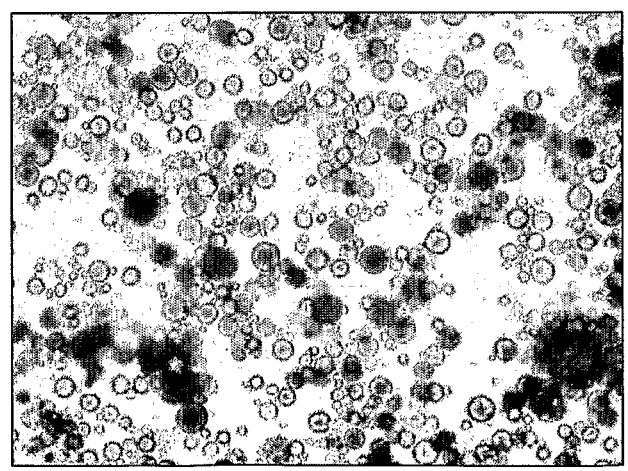
FIG. 12  50μm

MICROENCAPSULATION

This application is a 371 of International Application No. PCT/GB2009/000680 filed Mar. 13, 2009, which claims priority to GB 0804700.3 filed Mar. 13, 2008, the contents of which are incorporated herein by reference.

The present invention relates to a novel process for making microcapsules and to microcapsules made by the process. It also relates to a process for the use of the microcapsules.

Microcapsules are small capsules which comprise a wall which surrounds an encapsulated material, generally a liquid. They may be used for protecting the encapsulated material from the external environment, for example from degradation by air or light (especially u.v. radiation). They may also be used to isolate hazardous materials within the microcapsule to make them safer to handle or use. Microcapsules are known to be used for agrochemicals, particularly insecticides such as lambda cyhalothrin, to protect them from degradation by UV light and to provide controlled release following application.

Certain known microcapsules are made by interfacial polymerisation. In such a process a solution is first formed of a first monomer, such as a polyisocyanate, in a water-insoluble liquid to be encapsulated. The solution may also contain a biologically active ingredient. This solution is then dispersed in water together with surfactants to form an emulsion. A suitable second monomer such as a polyamine is added to the water and this reacts with the first monomer at the surface of the emulsion droplets to make a cross-linked polymer, in this example a polyurea, which forms a microcapsule wall around the droplets. Known first and second monomers also include polyisocyanate and polyol to make a polyurethane wall, polyfunctional acid halide and polyamine to make a polyamide wall and polyfunctional acid halide and polyol to make a polyester wall.

There are disadvantages of these types of microcapsules. Polymeric capsule walls of this known type provide poor protection for the contents from UV light. Also, the surfactant which is used to form the emulsion may lead to a problem when later handling the dispersion of microcapsules because it may cause foaming.

In one known approach, photoprotectants form part or all of the microcapsule wall materials and thus provide a shield for the capsule, thereby protecting any photosensitive active ingredient that is present within the capsules. For example CA2133779 shows that lignosulphonates and the like can be used in combination with a protein such as a high bloom gelatin to form a capsule wall that improves the resistance of agriculturally active substances, such as pesticides, to u.v. light degradation. The capsule wall formed by the interaction of these components is durable and has a u.v. protectant as an integral part of its structure.

Moy describes in EP539142A1 the use of colloidal inorganic particles, particularly those of silica and zirconium dioxide, to make microcapsules by coacervation or by interfacial polymerisation methods. The process involves the formation of so called Pickering emulsions and the thermoset microcapsule wall comprises the inorganic particles. Moy does not contemplate the use of surface-modified particles, not the use of cross-linkers to form the capsule wall.

Co-pending international application PCT/GB2007/003374 is concerned with light protecting particles which are chemically bonded to the microcapsule wall but does not contemplate microcapsule walls formed from light protecting particles themselves.

The present invention provides an aqueous dispersion of microcapsules having a cross-linked particulate inorganic wall in an aqueous medium. In a further aspect, these microcapsules may be further modified by adding, to the aqueous medium, a material which will further react with any remaining cross-linker. For example, when the cross-linker is a polyisocyanate, a polyamine such as diethylentriamine may be added. This causes further cross-linking and polymer formation at the microcapsule particulate inorganic wall and may be used to modify the durability of the capsules or permeability of the capsule walls to give, for example, a longer release time under given conditions.

BRIEF DESCRIPTION OF THE DRAWINGS

The invention will be better understood with reference to the detailed description when considered in conjunction with non-limiting examples and the accompanying drawings.

FIG. 1 is a light microscope image of the clay dispersion of Example 1.

FIG. 2 is a light microscope image of the Pickering emulsion of Example 2.

FIG. 2a is a light microscope image showing that the emulsion droplets collapse on drying in air on a glass slide.

FIG. 2b is a light microscope image showing the affect of addition of 5% by weight Synperonic™ NP8 to a Pickering emulsion.

FIG. 3 is a light microscope image of the microcapsules of Example 3.

FIG. 3a shows a stable microcapsule dispersion of FIG. 3.

FIG. 3b shows the microcapsules of FIG. 3 after the addition of Synperonic™ NP8.

FIG. 4 is a Scanning Electron Microscope image of the capsules of Example 4.

FIG. 5 is a light microscope image of the capsules of Example 5.

FIG. 5a is a light microscope image showing a stable microcapsule dispersion (Example 5) on drying on a glass microscope slide in air.

FIG. 5b is a light microscope image showing an unbroken capsule dispersion (Example 5) after the addition of Synperonic™ NP8.

FIG. 6a is a light microscope image of Example 6a.

FIG. 7 is a Scanning Electron Microscope image of Example 11a.

FIG. 11 is a light microscope image of capsules prepared according to Example 13 in their original dispersion.

FIG. 12 is a light microscope image of capsules prepared according to Example 13 in a dispersion formed from a redispersion after drydown.

Figure 6B:
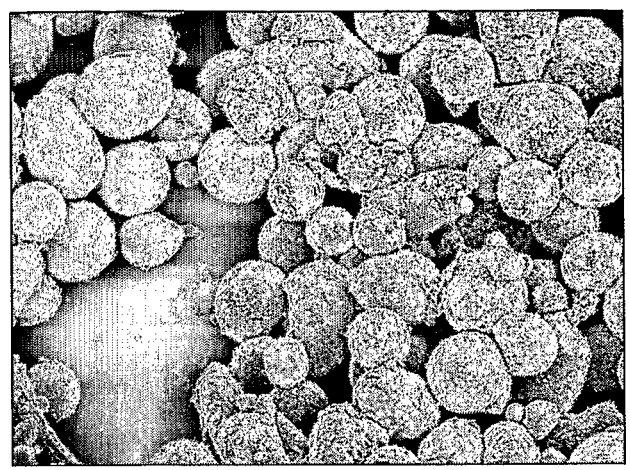
FIG. 6b is a Scanning Electron Microscope image of Example 6b.

The present invention relates to a new process for making microcapsules which does not require surfactant and which provides microcapsules having an increased, relatively high level of protection from u.v. light for the contents; the present invention involves the use of surface-modified particulate inorganic material to form microcapsule walls where a cross-linker is used to react with a reactive functional group on the surface-modified material such that each microcapsule wall is a cross-linked wall. The present invention does also allow surfactants to be used in the same formulation as a Pickering emulsion based system. Pickering emulsions are often destabilized by surfactants but in the present invention, cross-linking of the interfacial particles prevents this from occurring and surfactants may be safely added to the system once the interfacial cross-linking has occurred. Therefore, suitably, adjuvants may be built-in to microcapsule compositions of the present invention.

Microcapsules of the present invention are suitable for controlled release applications (for instance, controlled release of an active ingredient from within the core of the microcapsules). The controlled release rate may be tailored through the present invention.

Another aspect of the present invention is that the cross-linked systems may be easily modified through addition of an extra cross-linking molecule (for example, a water dispersible isocyanate or polyfunctional cross-linker, such as diethylenetriamine [DETA]) to the outer (external or continuous) phase of the dispersion such that the release rate of any active ingredient from within the core of the capsule may be varied to give a desired release rate profile. The opportunity to use extra cross-linking molecules means that it is possible to strengthen an existing layer in a single-layered capsule or to form multi-layered capsules.

The microcapsules of the present invention may be made by a process comprising:
i) forming a solution of a cross-linker in a liquid;
ii) forming a slurry of a surface-modified particulate inorganic material in an aqueous medium;
iii) dispersing the solution of step i) into the slurry of step ii) to form a Pickering emulsion and causing or allowing the cross-linker to react with a reactive functional group on the surface-modified particulate inorganic material so as to form a cross-linked microcapsule wall.

Steps (i) and (ii) may be carried out in any order.

A slurry is a suspension of a solid in a liquid; in this invention, the slurry formed in step is a suspension of cross-linkable, surface-modified inorganic particles in an aqueous-based medium. It has been found that it is possible to disperse the solution of step i) into the slurry of step ii) without using additional surfactants. This is because the particles of surface-modified inorganic material tend to accumulate at the interface between the solution droplets and the aqueous continuous phase and reduce the corresponding surface energy. This effect is known as a 'Pickering Emulsion'. The use of this combination of a Pickering Emulsion with a cross-linkable particulate inorganic material and a cross-linker allows for a particularly simplified process.

The liquid used in step i) comprises material to be encapsulated. In one embodiment, the liquid comprises an active ingredient which is to be encapsulated, optionally together with a solvent, particularly if at room temperature the active ingredient is a solid, or of high viscosity. Therefore, when present, the active ingredient may be the liquid, a part of the liquid, dissolved in the liquid, dispersed in the liquid or is a solid complex of an agrochemical with a molecular complexing agent and is dispersed in the liquid. The liquid is suitably substantially insoluble in water, more suitably it has a solubility in water at 20° C. of less than 10 g/l and most suitably less than 5 g/l. The liquid must dissolve the cross-linker so as to form a solution.

Any active ingredient encapsulated within the core of the microcapsules is suitably less than 10% by weight soluble in water and more suitably less than 1% by weight soluble in water; and most suitably less than 0.1% by weight soluble in water.

A wide range of active materials (active ingredients) may be encapsulated including inks, flavours, cosmetics, perfumes, sunscreens, fragrances, adhesives, sealants, phase change materials, biocides, oilfield chemicals (including corrosion and scale inhibitors), flame retardants, food additives (including vitamins, ingredients, probiotics and antioxidants), active agents that may be included in detergent, fabric softeners and other household products (such as bleaches, enzymes and surfactants), active agents that may be included in textiles (such as insect repellents, antimicrobial agents, skin softeners and medically active compounds), active agents that may be included in coatings (such as fire retardant, flame retardant, antifouling, antibacterial, biocidal, scratch resistant and abrasion resistant compounds) and biologically active compounds (such as pharmaceuticals and agrochemicals). Suitably the active material is an agrochemical such as a herbicide, fungicide or insecticide. Many such agrochemicals are known and are described in The Pesticide Manual 14th edition published by the British Crop Protection Council in 2006. The invention is also suitable for encapsulating a solid complex of an agrochemical with a molecular complexing agent including, for example, a complex of 1-MCP and α-cyclodextrin. The invention is most useful for agrochemicals that are subject to degradation when exposed to sunlight, in particular pyrethroid insecticides such deltamethrin, tralomethrin, cyfluthrin, alphamethrin, zeta-cypermethrin, fenvalerate, esfenvalerate, acrinathrin, allethrin, bifenthrin, bioallethrin, bioresmethrin, cycloprothrin, beta-cyfluthrin, cyhalothrin, beta-cypermethrin, cyphenothrin, empenthrin, etofenprox, fenpropathrin, flucythrinate, tau-fluvalinate, phenothrin, prallethrin, resmethrin, tefluthrin, tetramethrin, and lambda-cyhalothrin; suitably lambda-cyhalothrin.

Suitably, microcapsules of the present invention may be used in wall-boards or plasterboards in buildings, and may be used in improving cement compositions and processes for making cementitious materials.

The active ingredient is suitably a pharmaceutical compound or an agrochemical; more suitably it is an agrochemical.

Suitably, the agrochemical is a fungicide, insecticide, herbicide or growth regulator, used for controlling or combating pests such as fungi, insects and weeds or for controlling the growth of useful plants. The agrochemical may also be used in non-agricultural situations [for example public health and professional product purposes, such as termite barriers, mosquito nets and wall-boards].

Further suitable applications include, without limitation:

Sustained release or controlled release usages, for example: pharma, for example acid resistant capsules (oral delivery past low pH in the stomach), protection of labile actives, pseudo-zero order release through capsule wall and Ostwald-ripening resistant emulsion formulations; cosmetics; perfumes, for example slowing down evaporation of top-notes or sustained release and minimising overpowering odours; capsules having affinity for cellulose and trapped on textile surface during laundering; flavours, for example light stabilised to prevent oxidation; self-healing coatings, for example capsule bursts to release a resin that repairs damage; carbonless copy paper; novel, double taste and texture food, for example capsule which dissolves in the mouth and releases a new taste; pressure sensitive adhesives; sealants; nutrition (for example increased bioavailability of complex molecules and protection of sensitive molecules such as vitamins, probiotics and other food additives); toner inks with photosensitivity or thermal sensitivity; textile coatings, for example, for improving permeability properties; antifouling coatings; surface protective coatings, for example, for improving scratch or abrasion resistance; and construction materials, for example wall-boards, plasterboards and cements. Example of capsules that are dried out, include, for example, various mineral blends to form a ceramic upon calcination; low density fillers for polymers or paints; insulating materials; low density proppants; light reinforcing particles, for example for wood-fibre composites; recyclable pigments, for example low density allowing easy flotation separation; and energy buffers, for example use in a void in spheres to provide a 'crash barrier' with adsorption of energy. Capsules of the present invention may be of novel size or shape, for example: creation of plate or rod shape capsules; and use of metallic particles resulting in conductive capsules, or having a metallic nature, for example plasmon absorbance.

A solution suitable for use in step i) may be made by stirring a liquid and a cross-linker together. Heating and mechanical agitation may be used to aid or accelerate dissolution of the cross-linker. Similar techniques may be used to mix or dissolve an active ingredient with any solvent that is optionally included.

Examples of particulate inorganic materials are oxy-compounds [that is, oxygen based compounds] of at least one of calcium, magnesium, aluminium and silicon (or derivatives of such materials), such as silica, silicates, marble, clays and talc. Particulate inorganic materials may be either naturally occurring or synthesised in reactors. The particulate inorganic material may be a mineral chosen from, but not limited to, kaolin, bentonite, alumina, limestone, bauxite, gypsum, magnesium carbonate, calcium carbonate (either ground or precipitated), perlite, dolomite, diatomite, huntite, magnesite, boehmite, palygorskite, mica, vermiculite, hydrotalcite, hectorite, halloysite, gibbsite, kaolinite, montmorillonite, illite, attapulgite, laponite and sepiolite; suitably it may be chosen from kaolin, bentonite, alumina, limestone, bauxite, gypsum, magnesium carbonate, calcium carbonate (either ground or precipitated), perlite, dolomite, diatomite, huntite, magnesite, boehmite, sepiolite, palygorskite, mica, vermiculite, illite, hydrotalcite, hectorite, halloysite and gibbsite. Further suitable clays (for example aluminosilicates) include those comprising the kaolinite, montmorillonite or illite groups of clay mineral. Other specific examples are attapulgite, laponite and sepiolite.

In one aspect of the invention, the particulate inorganic material is kaolin clay. Kaolin clay is also referred to as china clay or hydrous kaolin, and is predominantly mineral kaolinite $(Al_2Si_2O_5(OH)_4)$, a hydrous aluminium silicate (or aluminosilicate).

The particulate inorganic material suitably has a particle size distribution wherein the median diameter $(d_{50})$ is less than or equal to 10 μm, as measured by determining the sedimentation speeds of the dispersed particles of the particulate material under test through a standard dilute aqueous suspension using a SEDIGRAPH™, for example SEDIGRAPH™ 5100, obtained from Micromeritics Corporation, USA. Suitably, the particulate inorganic material has a $d_{50}$ less than or equal to 5 μm. More suitably, the particulate inorganic material has a $d_{50}$ less than or equal to 2 μm. Yet more suitably, the particulate inorganic material has a $d_{50}$ less than or equal to 1 μm. In increasing suitability, the particulate inorganic material has a $d_{50}$ less than or equal to 0.9, 0.8, 0.7, 0.6, 0.5, 0.4, or 0.3 μm. In other aspects, the particulate inorganic material has a $d_{50}$ less than or equal to 0.2 μm, for example less than or equal to 0.15 μm or less than or equal to 0.12 μm or less than or equal to 0.1 μm.

In one aspect, at least about 90% of the particles of the particulate inorganic material by weight are smaller than about 2 μm, for example at least about 95% or 98% are smaller than about 2 μm. Suitably, at least about 90% of the particles by weight are smaller than about 1 μm, for example at least about 95% or 98% are smaller than about 1 μm. More suitably, at least about 75% of the particles by weight are smaller than about 0.25 μm, for example at least about 80% or 82% are smaller than about 0.25 μm. In another aspect, the particulate inorganic material has a particle size distribution of (i) at least about 90% of the particles by weight less than about 2 μm, for example at least about 95% or 98%; (ii) at least about 90% of the particles by weight are less than about 1 μm, for example at least about 95% or 98%; and (iii) at least about 75% of the particles by weight are less than about 0.25 μm, for example at least about 80% or 82%; and particulate inorganic material of such particle size distributions may also have $d_{50}$ values at the smaller end of the range, for example at least about 98% of the particulate inorganic material by weight is smaller than about 2 μm, at least about 98% is smaller than about 1 μm, at least about 82% is smaller than about 0.25 μm, and the $d_{50}$ value of the particulate inorganic material is less than or equal to 0.12 μm.

For finer particulate inorganic material (for example having a $d_{50}$ less than or equal to 2 μm), the material may be derived through classification, including methods such as gravity sedimentation or elutriation, use of any type of hydrocyclone apparatus or, for example, a solid bowl decanter centrifuge or a, disc nozzle centrifuge. The classified particulate inorganic material may be dewatered in one of the ways known in the art, for example filtration (including filter press), centrifugation or evaporation. The classified, dewatered material may then be thermally dried (for example, by spray drying).

Surface-modified means that the inorganic particle surface has been (chemically) modified so as to have cross-linkable, reactive functional groups. The surface of the particles may be modified using modifying agents selected from a wide variety of chemicals, with the general structure X—Y—Z, in which X is a chemical moiety with a high affinity for the particle surface; Z is a (reactive) chemical moiety with a desired functionality; and Y is a chemical moiety that links X and Z together. The term 'high affinity' relates to chemical moieties that are either chemically bonded or strongly physisorbed to the particle surface; suitably they are chemically bonded.

X may be, for example, an alkoxy-silane group such as tri-ethoxysilane or tri-methoxysilane, which is particularly useful when the particles have silanol (SiOH) groups on their surface. X may also be, for example, an acid group (such as a carboxylic or an acrylic acid group) which is particularly useful when the particles have basic groups on their surface.

Y may be any chemical group that links X and Z together, for example a polyamide, a polyester or an alkylene chain; more suitably it is an alkylene chain; and even more suitably it is a $C_{2-6}$ alkylene chain, such as ethylene or propylene.

Reactive groups Z may be selected from any groups, preferably different from Y, which can be used to react with a cross-linker so as to cross-link the surface modified particulate inorganic material. Examples of Z are epoxy groups, carboxylic groups, unsaturated groups such as acrylic or vinyl groups and, suitably, amine groups.

Suitable examples of surface modification rely on reaction of clay with aminosilanes, such as aminopropyltrimethoxysilane. The silane groups react with the clay so as to give free amine groups attached to the clay surface. An extensive range of silanes exists, able to modify surfaces with functionality appropriate for use in a range of polymer systems.

The reactive groups Z are reacted with a cross-linker so as to form a capsule wall. Cross-linkers are compounds that have at least two reactive groups that will react with the reactive groups on the surface-modified particles. Examples of cross-linkers that may be used to react with amine groups on a clay particle are polyisocyanates. Polyisocyanates provide a well-known class of cross-linker and include diisocyanates (such as toluene diisocyanate, hexamethylene diisocyanate and isophorone diisocyanate); isocyanates with, on average, more than two isocyanate groups (such as polymethylenepolyphenylene isocyanate); and many others including prepolymers of diisocyanates such as their reaction products with trimethylol propane and other simple polyols sold as Desmodur™ resins from Bayer.

Examples of cross-linkers that may be used to react with epoxy groups; with carboxylic groups; or with unsaturated groups such as acrylic or vinyl groups will be familiar to the person skilled in the art.

In one embodiment, clay is reacted with a suitable modifying agent, in the range of from 0.1 to 30% of the modifying molecule based on the weight of the clay (suitably in the range of from 0.1 to 20% and most suitably the range is from 0.1 to 10% by weight).

The aqueous medium suitable for use in step ii) mostly comprises water, for example by weight it is more than 80% water; and suitably more than 90% water. Optionally, the aqueous medium also comprises water miscible solvents, antifreeze agents or additional surfactants, although as mentioned above, these are not necessary. It has been found that surfactants may interfere with the formation of a Pickering emulsion and so it is preferred not to include surfactants at this stage.

A slurry suitable for use in step ii) may be made by agitating the particulate inorganic material in the aqueous medium using a mechanical stirrer (for example a Rotor/stator, Ystral™ or Ultra Turrax™) or by ultrasonic agitation. Suitably the slurry is agitated until the solution is added to it and the dispersion step is carried out.

In step iii), the solution may be dispersed in the slurry by conventional means such as ultrasonic dispersers or, suitably, high speed mechanical dispersers such as a Rotor/stator mixer, Ystral™ or Ultra Turrax™. The dispersion process is carried out for a period between 30 seconds and 20 minutes.

The dispersion step iii) results in a dispersion of the solution in the slurry which is stabilised as a Pickering emulsion by the surface-modified particulate inorganic material. This emulsion comprises droplets of the solution which are surrounded by and stabilised by the particles of the inorganic material. The cross-linker in the solution reacts with the reactive functional groups on the particulate inorganic material so as to form a cross-linked microcapsule wall. This reaction can be carried out simply by allowing the dispersion to stand at ambient temperature. Alternatively, the dispersion may be heated. The amount of time and the optimum temperature may be established by routine experimentation. Typically, when the particulate inorganic material is surface-modified so as to have amine groups on its surface and the cross-linker is a polyisocyanate, stirring the dispersion at between 15 and 25° C. for an hour is sufficient to complete the reaction.

The weight ratio of inorganic particle to solution phase will be from 1:0.1 to 1:40; suitably from 1:1 to 1:20.

The cross-linker may be used at a rate of from 0.1 to 30% w/w of the oil phase, more suitably from 0.5 to 20% and most suitably from 1 to 10%.

The reaction may be controlled by pH, temperature, addition of an electrolyte or by the use of a catalyst.

The process results in a dispersion of microcapsules in an aqueous medium. These microcapsules may be further modified by the addition to the aqueous medium of a material which will further react with any remaining cross-linker. For example, when the cross-linker is a polyisocyanate, a polyamine such as diethylentriamine may be added. This causes further cross-linking and polymer formation at the microcapsule wall and may be used to modify the durability of the capsules or permeability of the capsule walls to give, for example, a longer release time under given conditions.

The microcapsules may be isolated by drying, for example spray drying, to form a powder or may be used as the dispersion in the aqueous medium. When the microcapsules are isolated, they may be used dry or they may be redispersed in water before use.

The microcapsules made according to this process are new. According to the present invention there is provided a microcapsule comprising an encapsulated material surrounded by a wall, characterised in that the wall comprises a particulate inorganic material that has been surface-modified and cross-linked.

The invention is illustrated by the following Examples. The particulate inorganic material used in the Examples is a tabular (so called "blocky", flat or plate-like shape) ultrafine kaolin, having a $d_{50}$ of 0.12 μm and a particle size distribution with at least 98% of the particles by weight smaller than 1 μm and at least 82% smaller than 0.25 μm.

In these Examples, D[4,3] is the volume mean diameter of the relevant particles, capsules or droplets as obtained by laser light scattering of a diluted sample in a Malvern Mastersizer™ 2000.

Example 1

This Example illustrates the preparation of a surface-modified clay dispersion. Clay particles (ultrafine tabular Kaolin sourced in the USA, obtained from Imerys) were surface modified by the addition of 1.6% by weight aminopropyltriethoxysilane. The surface-modified particles were then added to water and dispersed with an Ultrasonic Probe (Sonics and Materials, Vibra Cell™, with microtip—hereinafter referred to as an Ultrasonic Probe) operated under the following conditions: 50% Duty cycle; Output Control 4; for 6 minutes. The composition is given in Table 1.

TABLE 1

| Ingredient | Concentration (% w/w) |
|---|---|
| clay (amino-silane modified, ultrafine tabular Kaolin) | 5 |
| Water | 95 |
| Total | 100 |

Results: Size of clay dispersion: D[4,3]=4.4 μm.

FIG. 1 is a light microscope image of the clay dispersion of Example 1.

Example 2

This Example illustrates the preparation of a simple Pickering emulsion.

Initially, Solvesso™ 200ND (aromatic oil from Exxon) was dispersed dropwise into the continuous phase of a modified Kaolin dispersion prepared according to Example 1, under high shear mixing with an Ystral™ high shear mixer (type X1020) with a two-pronged T10 head (hereinafter referred to as an Ystral™ high shear mixer) operated at about 5000 rpm. The concentrations of the ingredients used are given in Table 2.

Subsequent high shear mixing by the Ystral™ high shear mixer operated at about 20000 rpm for 2 minutes produced an oil in water [O/W] Pickering emulsion.

TABLE 2

| Ingredient | Concentration (% w/w) |
| --- | --- |
| 5% w/w clay (amino-silane modified, ultrafine tabular Kaolin) dispersion in water [from Example 1] | 85.7 |
| Solvesso ™ 200ND | 14.3 |
| Total | 100 |

Results: Size of emulsion droplets: D[4,3]=13 µm.

FIG. 2 is a light microscope image of the Pickering emulsion of Example 2.

FIG. 2a is a light microscope image showing that the emulsion droplets collapse on drying in air on a glass slide; the emulsion has broken.

FIG. 2b shows that the addition of 5% by weight Synperonic™ NP8 to the Pickering emulsion causes the emulsion to break after 4 days, as shown by light microscopy.

Example 3

This Example illustrates the preparation of a single-layered capsule suspension.

A solution of 5% w/w Suprasec™ 5025 (polymethylene polyphenylene isocyanate; PMPI) was prepared in Solvesso™ 200ND. Meanwhile, extra water was added to a surface-modified Kaolin dispersion prepared according to Example 1 and then to this dispersion, the Solvesso™ 200ND plus Suprasec™ 5025 solution was added dropwise with mixing by a Ystral™ high shear mixer operated at about 5000 rpm. The concentrations of the ingredients used are given in Table 3.

Subsequently, an oil in water [O/W] emulsion was prepared, by high shear mixing with the Ystral™ high shear mixer at about 20000 rpm for 2 minutes, which then developed into a microcapsule system as a cross-linking reaction took place.

TABLE 3

| Ingredient | Concentration (% w/w) |
| --- | --- |
| Solvesso ™ 200ND | 38 |
| Suprasec ™ 5025 | 2 |
| 5% w/w clay (amino-silane modified, ultrafine tabular kaolin) dispersion in water | 50 |
| Water | 10 |
| Total | 100 |

Results: Size of microcapsules: D[4,3]=20 µm.

FIG. 3 is a light microscope image of the microcapsules of Example 3. After ageing for at least 1 day, the microcapsules did not collapse upon drying on a glass microscope slide [see light microscope image, FIG. 3a, which shows a stable microcapsule dispersion] demonstrating that the wall had increased mechanical strength compared to the simple emulsion of Example 2. Addition of 5% w/w Synperonic™ NP8 did not cause the emulsion to break after a period of 1 week [see light microscope image, FIG. 3b, taken after the addition of Synperonic™ NP8 and showing unbroken capsule dispersion] demonstrating that cross-linking anchored the surface-modified clay at the interface such that it was not displaced by the surfactant. Pickering emulsions are usually incompatible with surfactants (as shown in FIG. 2b); cross-linking the particles allows them to be used with surfactants.

Example 4

This Example illustrates the preparation of a two-layered capsule suspension. Bayhydur™ 3100 [polyisocyanate based on hexamethylene diisocyanate modified with a polyether chain for water dispersibilty (from Bayer)] was dispersed in water by shaking and then the resultant Bayhydur™ 3100 solution was added dropwise to a single-layered capsule suspension prepared according to Example 3 with mixing from a Ystral™ high shear mixer at about 5000 rpm throughout the dropwise addition.

The resultant capsule suspension was then mixed with the Ystral™ high shear mixer at about 20000 rpm for 2 minutes. The composition is given in Table 4.

TABLE 4

| Ingredient | Concentration (% w/w) |
| --- | --- |
| 38% Solvesso ™ 200ND O/W EW with 2% Suprasec ™ 5025 (from Example 3) | 80 |
| Bayhydur ™ 3100 | 2 |
| Water | 18 |
| Total | 100 |

Result: The capsules remained intact during dry down and examination in a Scanning Electron Microscope, see FIG. 4, showing they had good mechanical strength. The Bayhydur™ 3100 can be seen as spheres attached to the outside of the capsule walls. The capsules were sufficiently strong for them to survive high shear mixing at 20000 rpm for 2 minutes with an Ystral™ high shear mixer.

Example 5

This Example illustrates the preparation of a single-layered capsule suspension with diethylenetriamine; it is similar to Example 3 but it has a second cross-linker.

A 25% w/w solution of diethylenetriamine (DETA) was prepared in water and then this aqueous DETA solution was added dropwise to a single-layered capsule suspension prepared according to Example 3 with mixing from an Ystral™ high shear mixer at about 5000 rpm. This capsule suspension was then mixed by the Ystral™ high shear mixer at about 20000 rpm for 2 minutes. The composition is given in Table 5.

TABLE 5

| Ingredient | Concentration (% w/w) |
| --- | --- |
| 38% Solvesso ™ 200ND O/W dispersion with 2% Suprasec ™ 5025 (Example 3) | 94.7 |
| Diethylenetriamine 25% w/w aqueous solution | 5.3 |
| Total | 100 |

Result: Size of capsules: D[4,3]=21 µm.

FIG. 5 is a light microscope image of the capsules of Example 5.

The capsules remained intact during either dry-down on a glass microscope slide or dry-down plus examination in a scanning electron microscope [SEM], demonstrating that they have good mechanical strength. The fact that there is no capsule collapse under SEM conditions demonstrates that the presence of the second cross-linker has enhanced the mechanical strength of the capsules compared to these of Example 3. The capsules were sufficiently strong for them to survive high shear mixing at 20000 rpm for 2 minutes with the Ystral™ high shear mixer.

FIG. 5a is a light microscope image showing a stable microcapsule dispersion (Example 5) on drying on a glass microscope slide in air.

FIG. 5b is a light microscope image showing an unbroken capsule dispersion (Example 5) after the addition of Synperonic™ NP8.

Example 6

This Example compares the release rate of non-cross-linked and cross-linked Pickering emulsions, compared to a polymer-stabilized emulsion.

Example 6a

This Example illustrates preparation of a simple Pickering emulsion.

A 50% by weight solution of dimethylphthalate in Solvesso™200ND was dispersed dropwise into a surface-modified Kaolin dispersion prepared according to Example 1, under high shear mixing with an Ystral™ high shear mixer at about 5000 rpm throughout the dropwise addition and an O/W emulsion was then prepared by high shear mixing with the Ystral™ high shear mixer at about 20000 rpm for 2 minutes. The composition is given in Table 6a.

TABLE 6a

| Ingredient | Concentration (% w/w) |
| --- | --- |
| Solvesso ™ 200ND | 20 |
| Dimethylphthalate | 20 |
| 5% w/w clay (amino-silane modified, ultrafine tabular kaolin) dispersion in water | 50 |
| Water | 10 |
| Total | 100 |

Result: Size of droplets: D[4,3]=43 μm.
FIG. 6a is a light microscope image of Example 6a.

Example 6b

This Example illustrates the preparation of a single-layered capsule suspension with diethylenetriamine containing dimethylphthalate prepared by an Ultrasonic process.

A 10% w/w Suprasec™ 5025, 45% w/w dimethyl phthalate and 45% w/w Solvesso™200ND solution was dispersed dropwise into a surface-modified kaolin dispersion prepared according to Example 1, under agitation with an Ultrasonic Probe;
and then an O/W emulsion was prepared by high shear mixing with the Ultrasonic Probe for 2 minutes, under the following conditions: 50% Duty cycle, Output Control 4. To this emulsion, a 25% w/w diethylenetriamine solution was added under mixing with the Ultrasonic Probe. The full composition is given in Table 6b.

TABLE 6b

| Ingredient | Concentration (% w/w) |
| --- | --- |
| Solvesso ™ 200ND | 17.1 |
| Dimethylphthalate | 17.1 |
| Suprasec ™ 5025 | 3.8 |
| 5% w/w clay (amino-silane modified, ultrafine tabular kaolin) dispersion in water | 47.4 |
| Water | 9.5 |
| Diethylenetriamine 25% w/w aqueous solution | 5.1 |
| Total | 100 |

Result: Size of capsules: D[4,3]=146 μm. (This size is very large, the reason being that, as seen in FIG. 6b, the capsules are sticking together). FIG. 6b is a Scanning Electron Microscope image of Example 6b.

Example 6c

This Example illustrates the preparation of a single-layered capsule suspension with diethylenetriamine containing dimethylphthalate, prepared with the high shear Ystral™ (or Ultra Turrax™) process of example 2.

A 10% w/w Suprasec™ 5025, 45% w/w dimethylphthalate and 45% w/w Solvesso™200ND solution was dispersed dropwise into a surface-modified kaolin dispersion prepared according to Example 1, under high shear mixing with an Ystral™ high shear mixer at about 5000 rpm; and an O/W emulsion was then prepared by high shear mixing with the Ystral™ high shear mixer at about 20000 rpm for 2 minutes. A 25% w/w diethylenetriamine solution was then added to the emulsion under mixing with the Ystral™ high shear mixer at about 5000 rpm and an O/W emulsion was then prepared by high shear mixing with the Ystral™ high shear mixer at about 20000 rpm for 2 minutes. The full composition is identical to that given in Table 6b; the difference between Example 6b and Example 6c lies in the preparation processes; ultrasonic and Ystral processes respectively.

Figure 6C:
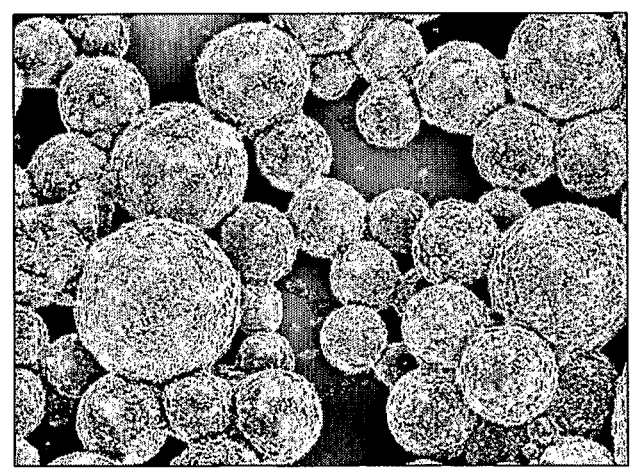
FIG. 6c is a Scanning Electron Microscope image of Example 6c.

Result: Size of capsules: D[4,3]=33 μm.
FIG. 6c is a Scanning Electron Microscope image of Example 6c.

Example 6d

This Example illustrates the preparation of a Mowiol™ 4-88 emulsion.

A 50% by weight solution of dimethyl phthalate in Solvesso™ 200ND was dispersed dropwise into a 2% w/w solution of Mowiol™ 4-88 (88% hydrolysed poly(vinyl acetate), MW ca. 28,000 Dalton), under high shear mixing with an Ystral™ high shear mixer. An O/W emulsion was then prepared by high shear mixing with the Ystral™ high shear mixer, the speed of which was adjusted to yield a droplet size about 20 μm. The full composition is given in Table 6d.

TABLE 6d

| Ingredient | Concentration (% w/w) |
| --- | --- |
| Solvesso ™ 200ND | 20 |
| Dimethylphthalate | 20 |
| 2% Mowiol ™ 4-88 aqueous solution | 60 |
| Total | 100 |

Result: Size of droplets: D[4,3]=17 µm.

Figure 6D:
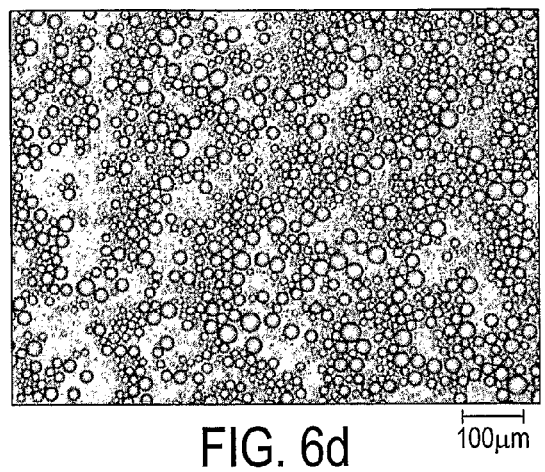
FIG. 6d is a light microscope image of Example 6d.

FIG. 6d is a light microscope image of Example 6d.

Example 6e

This Example provides release rate data for formulations prepared according to Examples 6a to 6d.

Figure 6E:
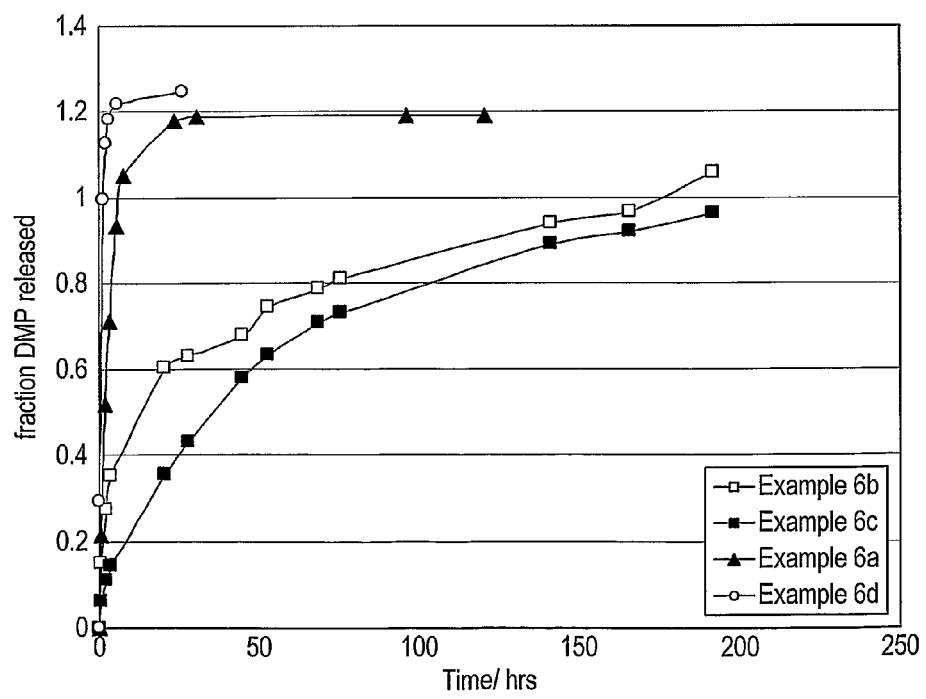
FIG. 6e shows release curves for formulations prepared according to Examples 6a to 6d.

Approximately 1 to 1.5 g of each of the four formulations described in Examples 6a-6d was diluted by a factor of 10 into water. Each of these solutions was placed in dialysis tubing and sealed in. Each dialysis tube was placed in ca. 100 ml of water and was then left on rollers in a temperature controlled room [temperature of 20(+/−2)° C.]. At suitable intervals, the UV absorbance of the water phase was measured at 276 nm with a Perkin Elmer™ UV spectrophotometer. This process allowed the release of dimethylphthalate [DMP] into water to be followed with time. Release curves shown below in FIG. 6e show that fast release was seen for dimethyl phthalate from the PVA stabilized emulsion (Example 6d) and from the unreacted clay stabilized emulsion (Example 6a). The rate of release was greatly reduced when the clay had been reacted with Suprasec™ 5025 (Example 6b) or with diethylenetriamine (Example 6c).

Example 7

This Example illustrates the preparation of a pre-dispersed surface-modified clay slurry. 30 g of surface-modified clay particles (as described in Example 1) were de-agglomerated (with a J&K mill) for 30 seconds prior to the addition of an equal weight of water. The slurry was homogenised using a Flack-Tek dispersing unit for 30 seconds. The slurry was later diluted with water to the desired concentration of 50% by weight for use in the following Examples.

Example 8

Examples 8, 9 and 10 illustrate the preparation of a single-layered capsule suspension containing a pesticide, lambda-cyhalothrin dissolved in Solvesso 200ND prepared with the high shear Ystral™ process. A Suprasec™ 5025, lambda-cyhalothrin and Solvesso™200ND solution was dispersed dropwise into a surface-modified kaolin dispersion prepared according to Example 7, under high shear mixing with an Ystral™ high shear mixer at about 2000 rpm; and an O/W emulsion was then prepared by high shear mixing with the Ystral™ high shear mixer at about 2000 rpm for 1 minute. A 25% w/w diethylenetriamine solution was then added to the emulsion under mixing with the Ystral™ high shear mixer at about 5000 rpm and an O/W emulsion was then prepared by high shear mixing with the Ystral™ high shear mixer at about 20000 rpm for 2 minutes. This emulsion formed a single-layer capsule dispersion. The full composition is given in Table 7.

TABLE 7

| Ingredient | Concentration (g) |
| --- | --- |
| Solvesso ™ 200ND | 18 |
| Lambda-cyhalothrin | 18 |
| Suprasec ™ 5025 | 4 |
| 5% w/w clay (amino-silane modified, ultrafine tabular kaolin) dispersion in water prepared by dilution of 50% clay paste of Example 7 in water. | 50 |
| Water | 10 |

Example 9

Example 9 is an example of a capsule product containing both a cross-linked bound clay particle and an extra polyurea binding layer. It was prepared by taking the emulsion of Example 8 and treating it with diethylenetriamine (cross-linker) in the quantities given in Table 8 and mixing under low shear to homogenise the product

TABLE 8

| Ingredient | Concentration/g |
| --- | --- |
| Diethylenetriamine [25% w/w aqueous solution] | 5 |
| Product from Example 8 | 100 |

Example 10

Example 10 is an example of a capsule product containing both a cross-linked bound clay particle and an extra polyurethane binding layer. It was prepared by taking the emulsion of Example 8 and treating it with glycerol (cross-linker) and DABCO (catalyst) in the quantities given in Table 9 and mixing under low shear to homogenise the product.

TABLE 9

| Ingredient | Concentration/g |
| --- | --- |
| Glycerol | 1 |
| DABCO [20% solution in water] | 0.5 |
| Product from Example 8 | 50 |

DABCO is (+−)-(E)-1-(2,6,6-trimethyl-2-cyclohexen-1-yl)-2-buten-1-one.

Examples 8, 9 and 10 immediately provided fluid dispersions that did not change on overnight standing. Further cross-linking was effected by heating the samples at 50° C. for 2 hours but the physical characteristics of the products did not change.

To test the compatibility of these products with further added components, an oil-in-water emulsion of a isoparaffinic oil (Isopar™ M) was prepared. Isopar M was dispersed dropwise into a 5% w/w solution of Gohsenol™ GL05 (88% hydrolysed poly(vinyl acetate)), under high shear mixing with an Ystral™ high shear mixer. An O/W emulsion was then prepared by high shear mixing with the Ystral™ high shear mixer, the speed of which was adjusted to yield a droplet size about 10 µm. The full composition is given in Table 10.

TABLE 10

| Ingredient | Concentration/g |
| --- | --- |
| Isopar M | 32 |
| 5% Gohsenol ™ GL05 aqueous solution | 50 |

Equal volumes of samples of each of Examples 8, 9 and 10 were then each independently mixed with an equal volume of the Isopar M emulsion. All the samples remained fluid both immediately and after standing for 24 hours, demonstrating the compatibility of products of the invention with an added oil-in-water emulsion.

Example 11

This Example provides data on enhancement seen in the photostability of lambda-cyhalothrin when trapped within Pickering capsules.

Example 11a

This Example illustrates the preparation of a single-layered capsule suspension with diethylenetriamine containing lambda cyhalothrin prepared with the high shear Ystral™ process. A 10% w/w Suprasec™ 5025, 47.5% w/w lambda cyhalothrin and 47.5% w/w Solvesso™200ND solution was dispersed dropwise into a surface-modified kaolin dispersion prepared according to Example 7, under high shear mixing with an Ystral™ high shear mixer at about 5000 rpm; and an O/W emulsion was then prepared by high shear mixing with the Ystral™ high shear mixer at about 20000 rpm for 2 minutes. This emulsion formed a single layer capsule dispersion. A 25% w/w solution of diethylenetriamine (DETA) was prepared in water and then this aqueous DETA solution was added dropwise to the single-layered capsule suspension with mixing from an Ystral™ high shear mixer at about 5000 rpm. This capsule suspension was then mixed by the Ystral™ high shear mixer at about 20000 rpm for 2 minutes. The full composition is given in Table 11.

TABLE 11

| Ingredient | Concentration (% w/w) |
| --- | --- |
| Solvesso ™ 200ND | 17 |
| Lambda-cyhalothrin | 17 |
| Suprasec ™ 5025 | 3.8 |
| 5% w/w clay (amino-silane modified, ultrafine tabular kaolin) dispersion in water (from Example 7) | 47.4 |
| Water | 9.5 |
| Diethylenetriamine 25% w/w aqueous solution | 5.3 |
| Total | 100 |

Result: Size: D[4,3]=31.7 μm.

Figure 7:
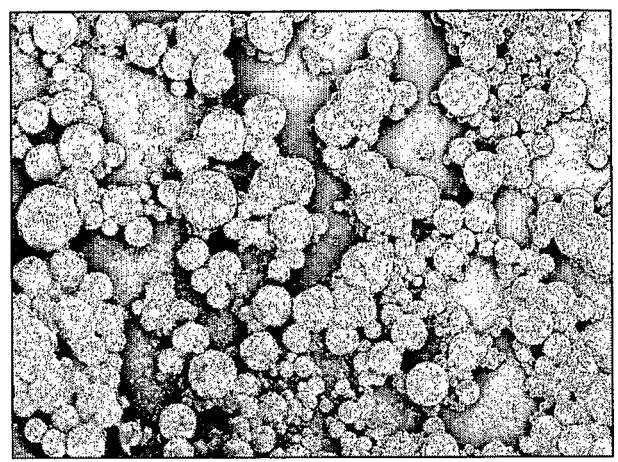

FIG. 7 is a Scanning Electron Microscope image of Example 11a.

Example 11b

This Example illustrates the preparation of a single-layered capsule suspension with diethylenetriamine containing lambda cyhalothrin prepared by the Ultrasonic process.

A 10% w/w Suprasec™ 5025, 45% w/w lambda cyhalothrin and 45% w/w Solvesso™200ND solution was dispersed dropwise into a surface-modified kaolin dispersion prepared according to Example 7, under agitation with an Ultrasonic Probe; and then an O/W emulsion was prepared by high shear mixing with the Ultrasonic Probe for 2 minutes; under the following conditions: 50% Duty cycle, Output Control 4. This emulsion formed a single layer capsule dispersion. To this capsule suspension, a 25% w/w diethylenetriamine solution was added under mixing with the Ultrasonic Probe. The full composition is given below in Table 12.

TABLE 12

| Ingredient | Concentration (% w/w) |
| --- | --- |
| Solvesso ™ 200ND | 17 |
| Lambda cyhalothrin | 17 |
| Suprasec ™ 5025 | 3.8 |
| 5% w/w clay (amino-silane modified, ultrafine tabular kaolin) dispersion in water (from Example 7) | 47.4 |
| Water | 9.5 |
| Diethylenetriamine 25% w/w aqueous solution | 5.3 |
| Total | 100 |

Figure 8:
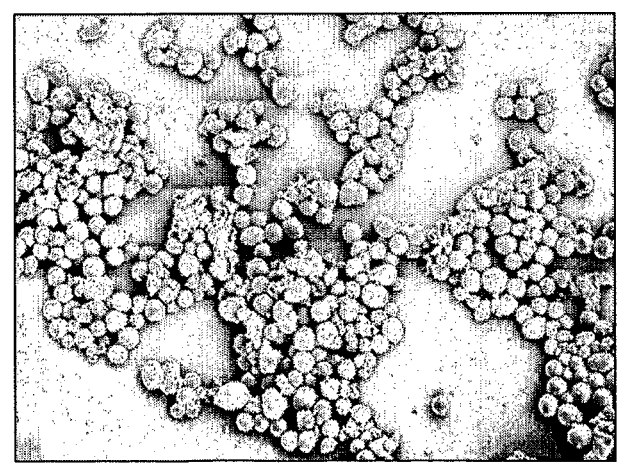
FIG. 8 is a Scanning Electron Microscope image of Example 11b.

FIG. 8 is a Scanning Electron Microscope image of Example 11b.

Result: Size of capsules: D[4,3]=171 μm (this is large due to aggregation of the capsules in the instrument, the electron micrograph shows the capsule size to be smaller).

Example 11c

Capsules according to Examples 11a and 11b were each assessed against commercially available capsules [Karate Zeon™] in a comparative study to determine the extent of protection provided by each of the capsules to lambda-cyhalothrin against u.v. photodegradation.

For each capsule type, samples of microcapsules were spread on glass slides and exposed to a xenon lamp (simulating sunlight) for up to three days. Using standard techniques, the microcapsules were analysed to determine the amount of lambda-cyhalothrin present in the formulations at the initiation of exposure to ultraviolet light and the amount remaining at various time periods during the three days' exposure.

Figure 9:
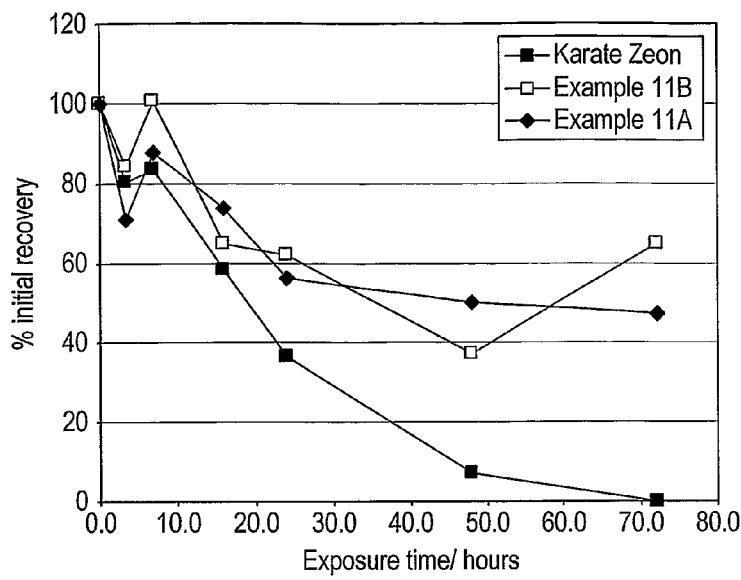
FIG. 9 shows the results of a comparative study of capsules prepared according to Examples 11a and 11b.

The results are shown in FIG. 9. The capsules of the present invention clearly provide better u.v. protection to lambda-cyhalothrin than does the current commercial product.

Example 12

This Example illustrates the preparation of a single-layered capsule suspension with diethylenetriamine containing dimethyl phthalate (which is an example of a volatile organic molecule) prepared with the high shear Ystral™ process. A 10% w/w Suprasec™ 5025, 47.5% w/w dimethyl phthalate and 47.5% w/w Solvesso™200ND solution was dispersed dropwise into a surface-modified kaolin dispersion prepared according to Example 7, under high shear mixing with an Ystral™ high shear mixer at about 5000 rpm; and an O/W emulsion was then prepared by high shear mixing with the Ystral™ high shear mixer at about 20000 rpm for 2 minutes. This emulsion formed a single layer capsule dispersion. The composition is given in Table 13.

TABLE 13

| Ingredient | Concentration (% w/w) |
| --- | --- |
| Solvesso 200ND | 18 |
| Dimethyl phthalate | 18 |

TABLE 13-continued

| Ingredient | Concentration (% w/w) |
|---|---|
| Suprasec 5025 | 4 |
| 5% clay dispersion in water (from Example 7) | 50 |
| Water | 10 |
| Total | 100 |

A 25% w/w solution of diethylenetriamine (DETA) was prepared in water and then varying amounts of this solution were added dropwise to the single-layered capsule suspension with mixing from an Ystral™ high shear mixer at about 5000 rpm) to give a range of DETA concentrations (0-1.3% by weight) in the final dispersions. Each capsule suspension was then mixed by the Ystral™ high shear mixer at about 20000 rpm for 2 minutes. The full composition is given in Table 14.

TABLE 14

| | Amount of DETA | | | | |
|---|---|---|---|---|---|
| | 0% Conc'n % w/w | 0.25% Conc'n % w/w | 0.5% Conc'n % w/w | 1% Conc'n % w/w | 1.3% Conc'n % w/w |
| 36% (Solvesso 200ND/ dimethyl phthalate) O/W EW with 4% Suprasec 5025 | 100 | 99.01 | 98 | 96.01 | 94.7 |
| Diethylenetriamine 25% w/w aq. solution | 0 | 0.99 | 2 | 3.99 | 5.3 |
| Total | 100 | 100 | 100 | 100 | 100 |
| Size: D[4, 3] (µm) | 21 | 37 | 40 | 33 | 30 |

Figure 10:
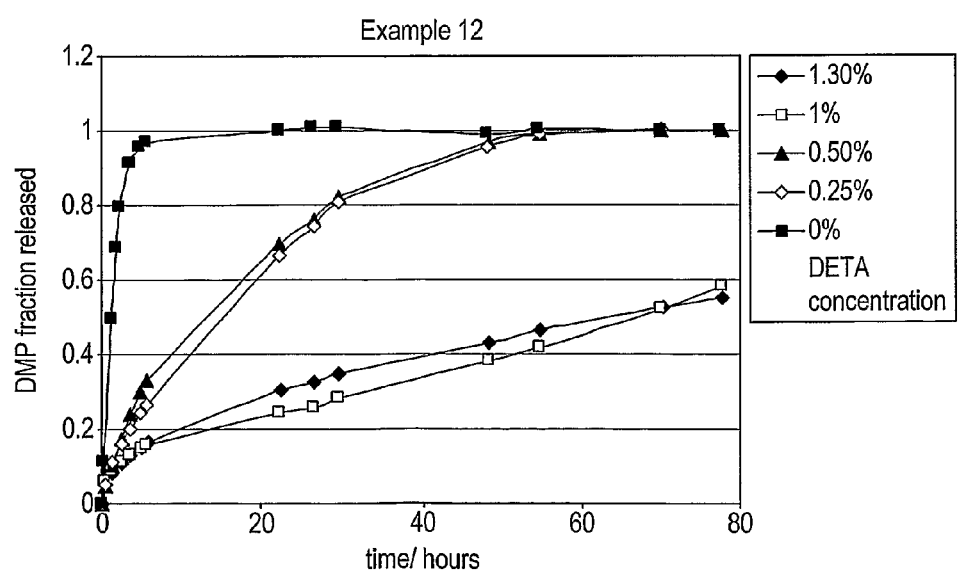
FIG. 10 shows the release rate of dimethylphthalate [DMP] into water of capsules prepared according to Example 12.

Approximately 1 to 1.5 g of each of these capsule formulations was diluted by a factor of 10 into water. Each of these dilutions was placed in dialysis tubing and sealed in. Each dialysis tube was placed in about 100 ml of water and was then left on rollers in a temperature controlled room [temperature of 20(+/−2)° C.]. At suitable intervals, the UV absorbance of the water phase was measured at 276 nm with a Perkin Elmer™ UV spectrophotometer. This process allowed the release of dimethylphthalate [DMP] into water to be followed with time; see FIG. 10, which shows that increasing the DETA loading decreases the rate of release of DMP from the capsules, showing that the rate of release is readily controlled by the loading of DETA used in the formulation.

Example 13

This Example illustrates the preparation of a single-layered capsule suspension with diethylenetriamine containing mefenoxam prepared with the high shear Ystral™ process. The capsule dispersion was found to show good redispersion properties after drying down to a dry deposit. A 5% w/w Suprasec™ 5025, 47.5% w/w mefenoxam and 47.5% w/w Solvesso™200ND solution was dispersed dropwise into a surface-modified kaolin dispersion prepared according to Example 7, under high shear mixing with an Ystral™ high shear mixer at about 5000 rpm; and an O/W emulsion was then prepared by high shear mixing with the Ystral™ high shear mixer at about 20000 rpm for 2 minutes. This emulsion formed a single layer capsule dispersion. A 25% w/w solution of diethylenetriamine (DETA) was prepared in water and then this aqueous DETA solution was added dropwise to the single-layered capsule suspension with mixing from an Ystral™ high shear mixer at about 5000 rpm. This capsule suspension was then mixed by the Ystral™ high shear mixer at about 20000 rpm for 2 minutes. The full composition is given in Table 15.

TABLE 15

| Ingredient | Concentration (% w/w) |
|---|---|
| Solvesso ™ 200ND | 18 |
| Mefenoxam | 18 |
| Suprasec ™ 5025 | 1.9 |
| 5% w/w clay (amino-silane modified, ultrafine tabular kaolin) dispersion in water | 47.4 |
| Water | 9.5 |
| Diethylenetriamine 25% w/w aqueous solution | 5.2 |
| Total | 100 |

Result: Size of capsules: D[4,3]=13.7 µm.

This formulation gave capsules that were stable on dry down, and the capsules in the aqueous dispersion were stable over a period of 9 months at ambient temperature. A sample of this dispersion was allowed to dry down in a plastic tray in a fume hood for 3 days, after which it was found to redisperse readily in water with gentle agitation. FIG. 11 shows the capsules in their original dispersion and FIG. 12 shows them in the dispersion formed from the redispersion after dry down. The capsules appeared to have lost some of the more volatile Solvesso™ 200ND through evaporation, but the capsules remained essentially intact and showed facile redispersion.

The invention claimed is:

1. A process for making microcapsules comprising:
   i) forming a solution of a cross-linker in a liquid;
   ii) forming a slurry of a surface-modified particulate inorganic material in an aqueous medium; and
   iii) dispersing the solution in the slurry and causing or allowing the cross-linker to react with the surface-modified particulate inorganic material so as to form a microcapsule comprising a cross-linked particulate inorganic microcapsule wall,
   wherein the surface-modified particulate inorganic material is clay which has been surface-modified with an amino-silane.

2. A process as claimed in claim 1 in which the liquid that is used to form a solution of the cross-linker is substantially insoluble in water.

3. A process as claimed in claim 2 in which the liquid that is used to form a solution of the cross-linker has a solubility in water at 20° C. of less than 10 g/l.

4. A process as claimed in claim 1 in which the liquid that is used to form a solution of the cross-linker further comprises an active material which is an agrochemical.

5. A process as claimed in claim 4 in which the active material is an insecticide.

6. A process as claimed in claim 5 in which the insecticide is a pyrethroid.

7. A process as claimed in claim 6 in which the pyrethroid is lambda-cyhalothrin.

8. A process as claimed in claim 1 in which the particulate inorganic material comprises an oxy-compound of a metal selected from the group consisting of calcium, magnesium, aluminum, silicon, and combinations thereof.

9. A process as claimed in claim 1 in which the particulate inorganic material has a median diameter ($d_{50}$) less than or equal to 10 µm.

10. A process as claimed in claim 1 in which the particulate inorganic material has a particle size distribution where at least about 90% of the particles by weight are smaller than about 2 μm.

11. A process as claimed in claim 1 in which the particulate inorganic material has a particle size distribution where at least about 90% of the particles by weight are less than about 2 μm and at least about 75% of the particles by weight are less than about 0.25 μm.

12. A process as claimed in claim 1 in which the aminosilane with which the particulate inorganic material has been modified has a chemical structure of X—Y—Z, in which X is a chemical moiety with a high affinity for the particle surface; Z is an amine group and Y is a chemical moiety that links X and Z together.

13. A process as claimed in claim 12 in which X is an alkoxy-silane group.

14. A process as claimed in claim 12 in which Y is a $C_{2-6}$ alkylene chain.

15. A process as claimed in claim 1 in which the cross-linker is a polyisocyanate.

16. A process as claimed in claim 1 where the cross-linked microcapsule wall is modified through addition of an extra cross-linking molecule during or after step (iii).

17. A process as claimed in claim 1 in which the particulate inorganic material is natural.

18. A process as claimed in claim 1 in which the particulate inorganic material is synthetic.

* * * * *